(12) United States Patent
Zou et al.

(10) Patent No.: US 11,098,049 B2
(45) Date of Patent: Aug. 24, 2021

(54) SYNTHETIC METHOD FOR BENZIMIDAZO[1,2-C]QUINAZOLIN-6-ONES

(71) Applicant: Jiangnan University, Wuxi (CN)

(72) Inventors: Lianghua Zou, Wuxi (CN); Fei Ren, Wuxi (CN); Biao Liu, Wuxi (CN); Kai Shi, Wuxi (CN); Cheng Yan, Wuxi (CN); Shuai Zhu, Wuxi (CN); Hao Zhu, Wuxi (CN); Yuhao Cheng, Wuxi (CN); Zhekang Jia, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/113,444

(22) Filed: Dec. 7, 2020

(65) Prior Publication Data

US 2021/0087199 A1 Mar. 25, 2021

Related U.S. Application Data

(63) Continuation of application No. PCT/CN2020/085634, filed on Apr. 20, 2020.

(30) Foreign Application Priority Data

Jul. 25, 2019 (CN) .......................... 201910675411.3

(51) Int. Cl.
*C07D 487/04* (2006.01)

(52) U.S. Cl.
CPC ................. *C07D 487/04* (2013.01)

(58) Field of Classification Search
CPC .......................... C07D 487/04; A61K 31/519
USPC ........................................ 544/247; 514/259.5
See application file for complete search history.

(56) References Cited

FOREIGN PATENT DOCUMENTS

KR 20150037703 A 4/2015

OTHER PUBLICATIONS

Yang Fang et al., Synthesis of Benzimidazo[1,2-c]quinazoline Derivatives induced by low-valent titanium reagent, Journal of Xuzhou Normal University (Natural Science), vol. 30, No. 1, pp. 61-64, Mar. 15, 2012 (Mar. 15, 2012).
Ping-Gui Li et al., Direct construction of benzimidazo[1, 2-c]quinazolin-6-ones via metal-free oxidative C—C bond cleavage. Organic Chemistry Frontiers. Oct. 25, 2018, vol. 23, No. 5, p. 3464-3468.

*Primary Examiner* — Jeffrey H Murray
(74) *Attorney, Agent, or Firm* — IPro, PLLC; Na Xu

(57) ABSTRACT

The disclosure discloses a synthetic method for benzimidazo[1,2-c]quinazolin-6-ones and belongs to the field of organic synthesis. In the disclosure, an α-ketoamide compound shown as Formula I and an o-phenylenediamine compound shown as Formula II are used as substrates and undergo a reaction under the action of a catalyst and a base to obtain benzimidazo[1,2-c]quinazolin-6-ones shown as Formula III. In the disclosure, benzimidazo[1,2-c]quinazolin-6-ones are prepared based on a novel and efficient action mechanism, and the disclosure has the advantages that the raw materials are cheap, the catalyst is cheap and easy to obtain, the reaction is efficient and environmentally friendly, the substrate range is wide, the yield is high, and the operation is simple.

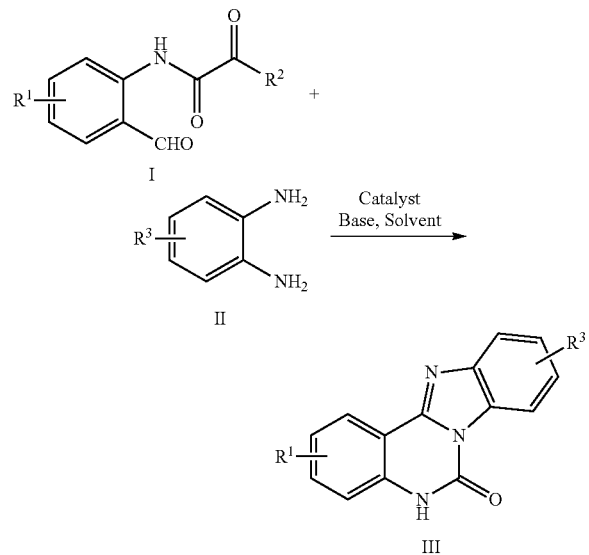

13 Claims, No Drawings

SYNTHETIC METHOD FOR BENZIMIDAZO[1,2-C]QUINAZOLIN-6-ONES

TECHNICAL FIELD

The disclosure belongs to the field of organic synthesis and specifically relates to a synthetic method for benzimidazo[1,2-c]quinazolin-6-ones.

BACKGROUND

Quinazolinone is an important aromatic heterocyclic compound with a benzopyrimidinone structure, which has the advantages of low toxicity, high efficiency, unique action mode and the like. The design, synthesis and biological activity research of such a compound have become a very active field of medical research and received widespread attention. Many quinazolinone compounds such as methaqualone and piriqualone (anticonvulsant drug), raltitrexed (anticancer drug) and ketanserin (antihypertensive drug) have been widely used in clinical practice. In recent years, quinazolinone compounds have shown a great development potential in the antibacterial field and antifungal field. At the same time, azole compounds such as imidazole, triazole, tetrazole, benzene ring-fused benzimidazole and benzotriazole and other nitrogen-containing aromatic heterocycles can interact with effect targets such as enzymes and receptors in a variety of organisms due to unique structures, and can adjust and improve the physicochemical properties and pharmacokinetic properties of active molecules.

Benzimidazo[1,2-c]quinazolin-6-one is the core skeleton structure of biologically active substances, synthetic drugs and natural drugs, and has a wide range of applications in biology and pharmacology research. In addition, this structural unit is widely present in antibacterial agents, antibacterial agent precursors and inhibitors such as cholinesterase, and is also a key intermediate for the synthesis of some important compounds. The existing synthesis of benzimidazo[1,2-c]quinazolin-6-ones has been reported, this compound is obtained by a reaction of isatin and phenylenediamine under conditions of DMSO, $O_2$ and 130° C. and is difficult to separate, and the yield is low.

SUMMARY

The disclosure discloses a synthetic method for benzimidazo[1,2-c]quinazolin-6-ones, and the synthetic route is as follows:

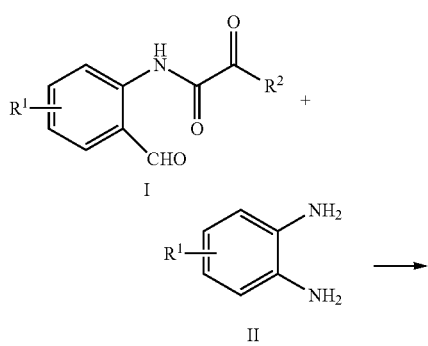

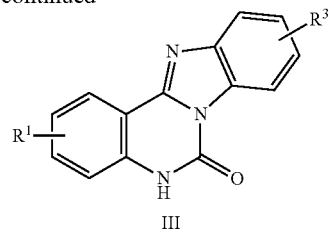

wherein, $R^1$ and $R^3$ are independently selected from unsubstituted or halogen-substituted C1-C8 alkyl, halogen, C1-C8 alkoxy, unsubstituted or halogen-substituted C1-C8 cycloalkyl, unsubstituted aryl, and halogen, alkyl or alkoxy-substituted aryl, respectively; $R^2$ is selected from unsubstituted or substituted aryl and unsubstituted or substituted aromatic heterocyclic group, and the substituent group on the aryl or aromatic heterocyclic group includes halogen, alkyl and alkoxy.

An α-ketoamide compound shown as Formula I and an o-phenylenediamine compound shown as Formula II undergo a reaction in an organic solvent under the action of a catalyst and a base to obtain benzimidazo[1,2-c]quinazolin-6-ones shown as Formula III.

In an embodiment of the disclosure, $R^1$ is preferably unsubstituted C1-C4 alkyl, halogen or C1-C4 alkoxy.

In an embodiment of the disclosure, $R^2$ is preferably the groups of the following structures:

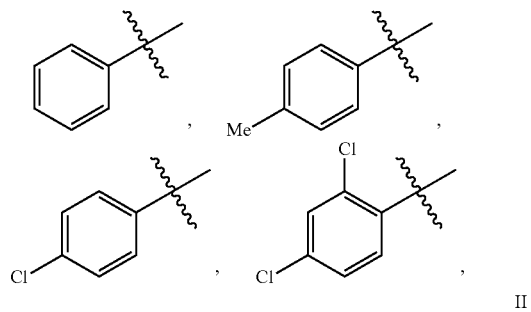

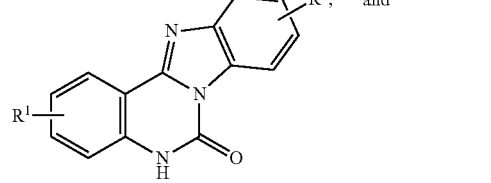

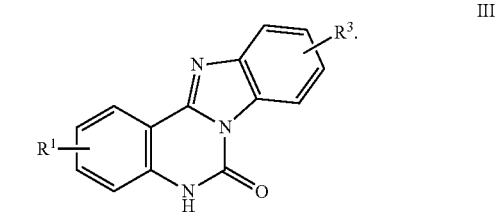

In an embodiment of the disclosure, $R^3$ is preferably unsubstituted C1-C4 alkyl or halogen, more preferably F, Cl, Br or Me.

In an embodiment of the disclosure, according to the method, the reaction is carried out in an air atmosphere under the action of a catalyst and a base.

In an embodiment of the disclosure, the organic solvent includes one or more of N,N-dimethylformamide, acetonitrile, ethanol, methanol or 1,2-dichloroethane.

In an embodiment of the disclosure, the catalyst is a copper catalyst, including cuprous iodide, cuprous bromide, copper acetate, copper bromide, copper powder, copper trifluoromethanesulfonate and anhydrous copper sulfate.

In an embodiment of the disclosure, the catalyst is preferably a divalent copper catalyst, more preferably copper bromide.

In an embodiment of the disclosure, the base is a strong base, including cesium carbonate, potassium carbonate and potassium phosphate, preferably cesium carbonate.

In an embodiment of the disclosure, the reaction temperature is 100-150° C., and the reaction time is 22-26 hours.

In an embodiment of the disclosure, the ratio of amount of substance of α-ketoamide shown as Formula I to o-phenylenediamine shown as Formula II is 1.0:(0.85-0.95).

In an embodiment of the disclosure, the ratio of amount of substance of α-ketoamide shown as Formula I to the catalyst to the base is 1:(0.05-0.15):(2.5-3.5).

In an embodiment of the disclosure, based on the amount of substance of α-ketoamide shown as Formula I, the addition amount of the organic solvent is 6-14 mL/mmol.

In an embodiment of the disclosure, after the reaction, a silica gel column is used for chromatography and separation to purify the product.

In an embodiment of the disclosure, a purification method includes the steps that after the reaction is completed, column chromatography silica gel is added, the solvent is removed by vacuum distillation, the silica gel column is spin-dried until silica gel adsorbs the powdery product, and a sample is added onto the column, eluted with the mixture of petroleum ether and ethyl acetate, collected and concentrated by evaporation to obtain benzimidazo[1,2-c]quinazolin-6-ones.

The disclosure also discloses benzimidazo[1,2-c]quinazolin-6-ones, having the structure shown as Formula III below:

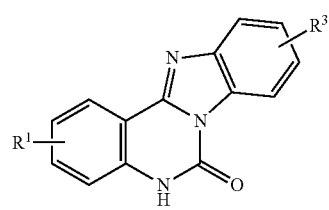

III wherein, $R^1$ and $R^3$ are independently selected from unsubstituted or halogen-substituted C1-C8 alkyl, halogen, C1-C8 alkoxy, unsubstituted or halogen-substituted C1-C8 cycloalkyl, unsubstituted aryl, and halogen, alkyl or alkoxy-substituted aryl, respectively.

Compared with the prior art and the previously reported synthesis of benzimidazo[1,2-c]quinazolin-6-ones, the disclosure has the following advantages that firstly, only a single catalyst is needed, the catalyst is cheap and easy to obtain, the amount used is low, the copper catalyst is only 0.1 equivalent, the catalytic efficiency is high, the product yield is 47% or above, the product is easy to separate and purify, and the substrate universality is good. A variety of biologically active molecules and skeleton molecules thereof have been synthesized by this method. Therefore, it is of great significance to develop a synthetic method of benzimidazo[1,2-c]quinazolin-6-ones.

DETAILED DESCRIPTION

The technical scheme of the disclosure will be further described in detail below in conjunction with specific examples.

The halogen referred to in the disclosure refers to fluorine, chlorine, bromine and iodine; C1-C8 alkyl refers to straight or branched chain alkyl with 1-8 carbon atoms; alkoxy refers to a group with the structure —OR, wherein R is C1-C8 alkyl; and aryl refers to a phenyl or naphthyl group.

The aromatic heterocyclic group refers to a mono- or bicyclic aromatic ring system having 5 to 12 ring atoms, wherein at least one atom in the ring system is a heteroatom selected from N, O and S. This definition also includes ring systems in which heteroaryl groups are fused with benzene rings. Examples of suitable "heteroaryl rings" or "heteroaryl groups" are benzimidazolyl, benzofuranyl, benzothienyl, benzoxazolyl, benzothiazolyl, benzotriazolyl, benzotetrazolyl, benzisoxazolyl, benzisothiazolyl, quinolyl, furanyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl and thienyl.

The raw material α-ketoamide compound used in the disclosure can be prepared according to existing documents, such as document Li, P.-G.; Zhu, H.; Fan, M.; Yan, C.; Shi, K.; Chi, X.-W.; Zou, L.-H. Org. Biomol. Chem. 2019, 17, 5902-5907. The specific synthetic method is as follows:

2,1-benzisoxazole (0.3 mmol, 41.1 mg), benzoylformic acid (0.6 mmol, 90.1 mg), and CuBr(PPh$_3$)$_3$ (0.015 mmol, 13.9 mg) are added into a 25 ml schlenk tube, and argon is used replacement for the reaction tube three times under reduced pressure. 1,2-dichloroethane (3 ml) is added, and the mixture is stirred at 110° C. for 12 hours. After the reaction is completed, 100-200 mesh column chromatography silica gel is added, the solvent is removed by vacuum distillation, a crude product is subjected to silica gel column chromatography and separation and eluted with a mixture of petroleum ether and ethyl acetate (petroleum ether:ethyl acetate=20:1), elution is carried out by means of TLC for tracking detection, and the eluent containing the target product is collected, combined and concentrated by evaporation to obtain the α-ketoamide compound with an ortho-aldehyde group shown as Formula I.

The synthetic route is as follows:

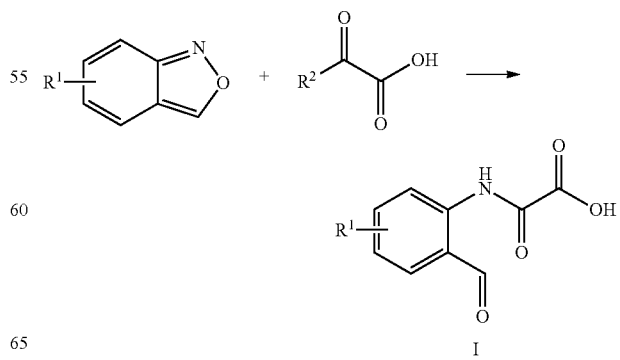

I

In some examples of the disclosure, R¹ is H, OMe, F, Cl, Br or CF$_3$;

R² is

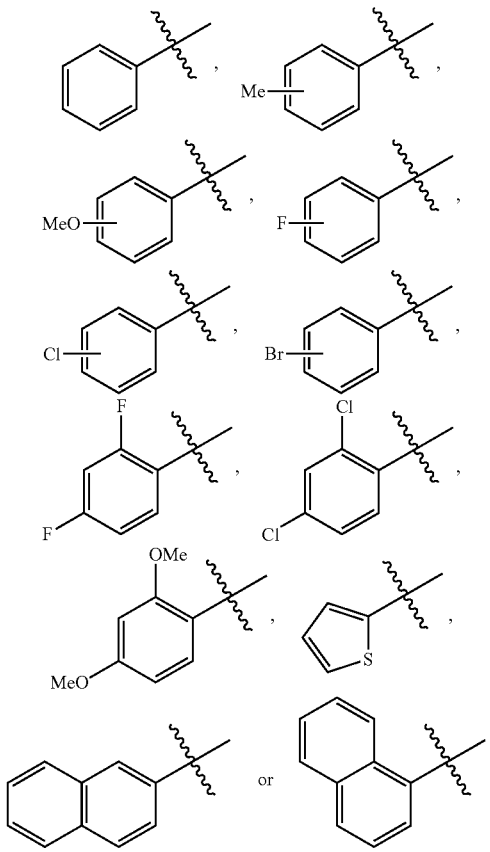

Both the raw materials including o-phenylenediamine compounds and benzisoxazole compounds with substituent groups used in the disclosure can be purchased commercially.

Example 1

The structural formula of the benzimidazoquinazolinone compound prepared in this embodiment is as follows:

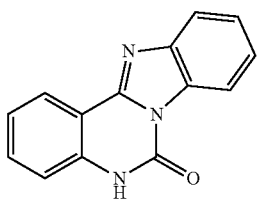

III-1

To a 25 mL sealed tube equipped with a magnetic stirring bar was added N-(2-Formylphenyl)-2-oxo-2-phenylacetamide (0.23 mmol, 58.2 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-1 in 81% yield (white solid).

Characterization data: ¹H NMR (400 MHz, DMSO-d$_6$) δ 11.98 (s, 1H), 8.35 (dd, J=18.2, 7.6 Hz, 2H), 7.87 (d, J=7.7 Hz, 1H), 7.67 (t, J=7.3 Hz, 1H), 7.54-7.34 (m, 4H); ¹³C NMR (101 MHz, DMSO-d$_6$) δ 148.2, 146.9, 144.0, 137.6, 132.8, 131.1, 125.5, 124.9, 124.1, 123.9, 119.6, 116.4, 115.2, 112.3.

Example 2

The structural formula of the benzimidazoquinazolinone compound prepared in this embodiment is as follows:

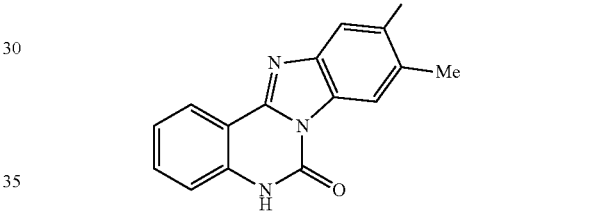

III-2

To a 25 mL sealed tube equipped with a magnetic stirring bar was added N-(2-Formylphenyl)-2-oxo-2-phenylacetamide (0.23 mmol, 58.2 mg), 4,6-dimethyl-1,2-phenylenediamine (0.2 mmol, 27.2 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg, 3.0 equiv.) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-2 in 47% yield (light yellow solid).

Characterization data: ¹H NMR (400 MHz, DMSO-d$_6$) δ 11.90 (s, 1H), 8.27 (dd, J=7.8, 1.0 Hz, 1H), 8.12 (s, 1H), 7.67-7.59 (m, 2H), 7.36 (dd, J=14.2, 7.5 Hz, 2H), 2.40 (s, 3H), 2.38 (s, 3H); ¹³C NMR (101 MHz, DMSO-d$_6$) δ 147.3, 146.8, 142.5, 137.3, 134.1, 133.0, 132.4, 129.4, 124.7, 123.8, 119.6, 116.3, 115.2, 112.4, 20.6, 20.6.

Example 3

The structural formula of the benzimidazoquinazolinone compound prepared in this embodiment is as follows:

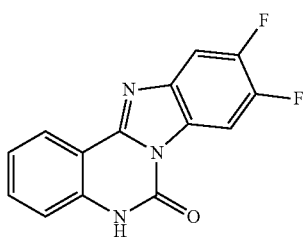

III-3

To a 25 mL sealed tube equipped with a magnetic stirring bar was added N-(2-Formylphenyl)-2-oxo-2-phenylacetamide (0.23 mmol, 58.2 mg), 1,2-diamino-4,5-difluorobenzene (0.2 mmol, 28.8 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg, 3.0 equiv.) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-3 in 76% yield (light yellow solid).

Characterization data: $^1$H NMR (400 MHz, DMSO) δ 12.08 (s, 1H), 8.32-8.10 (m, 2H), 7.99-7.89 (m, 1H), 7.66 (t, J=7.3 Hz, 1H), 7.49-7.27 (m, 2H); $^{13}$C NMR (101 MHz, CDCl$_3$) δ 154.67, 154.55 (d, J=2.9 Hz), 152.20 (d, J=14.4 Hz), 152.09 (dd, J=241.1, 14.4 Hz), 151.20, 144.50 (d, J=11.1 Hz), 142.36, 137.77, 130.38 (dd, J=174.4, 10.3 Hz), 128.75, 121.23, 112.10 (dd, J=20.1, 3.9 Hz), 116.71, 108.11 (dd, J=23.9, 10.1 Hz); $^{19}$F NMR (376 MHz, CDCl$_3$) δ −135.49 (d, J=15.0 Hz), −136.28 (d, J=14.5 Hz); HRMS m/z (ESI-TOF) calcd for C$_{14}$H$_8$F$_2$N$_3$O (M+H)$^+$ 272.0630, found 272.0625.

Example 4

The structural formula of the benzimidazoquinazolinone compound prepared in this embodiment is as follows:

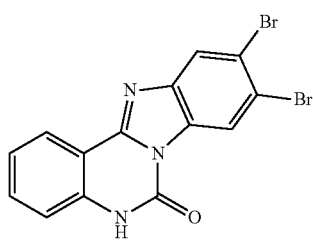

III-4

To a 25 mL sealed tube equipped with a magnetic stirring bar was added N-(2-Formylphenyl)-2-oxo-2-phenylacetamide (0.23 mmol, 58.2 mg), 4,5-dibromo-1,2-phenylenediamine (0.2 mmol, 52.8 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg, 3.0 equiv.) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-4 in 60% yield (brownish yellow solid).

Characterization data: $^1$H NMR (400 MHz, DMSO-d$_6$) δ 12.13 (s, 1H), 8.57 (s, 1H), 8.29-8.19 (m, 2H), 7.74-7.63 (m, 1H), 7.37 (t, J=7.7 Hz, 2H); $^{13}$C NMR (101 MHz, DMSO-d$_6$) δ 150.0, 146.4, 144.42, 137.9, 133.4, 131.3, 125.1, 124.1, 123.9, 120.0, 119.2, 118.0, 116.5, 111.8; HRMS m/z (ESI-TOF) calcd for C$_{14}$H$_2$Br$_2$N$_3$O (M+H)$^+$ 391.9029, found 391.9041.

Example 5

The structural formula of the benzimidazoquinazolinone compound prepared in this embodiment is as follows:

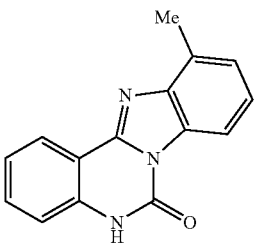

III-5

To a 25 mL sealed tube equipped with a magnetic stirring bar was added N-(2-Formylphenyl)-2-oxo-2-phenylacetamide (0.23 mmol, 58.2 mg), 3-methyl-1,2-phenylenediamine (0.2 mmol, 24.4 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg, 3.0 equiv.) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-5 in 56% yield (brownish yellow solid).

Characterization data: $^1$H NMR (400 MHz, DMSO-d$_6$) δ 11.92 (s, 1H), 8.31 (d, J=7.7 Hz, 1H), 8.16 (d, J=7.6 Hz, 1H), 7.63 (t, J=7.6 Hz, 1H), 7.47-7.22 (m, 4H), 2.66 (s, 3H); $^{13}$C NMR (101 MHz, DMSO-d$_6$) δ 147.3, 146.9, 143.1, 137.5, 132.5, 130.6, 129.1, 125.6, 124.9, 124.0, 123.7, 116.3, 112.6, 112.4, 17.1.

Example 6

The structural formula of the benzimidazoquinazolinone compound prepared in this embodiment is as follows:

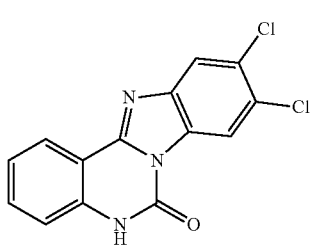

III-6

To a 25 mL sealed tube equipped with a magnetic stirring bar was added N-(2-Formylphenyl)-2-oxo-2-phenylacetamide (0.23 mmol, 58.2 mg), 4,5-dichloro-1,2-benzenediamine (0.2 mmol, 52.8 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg, 3.0 equiv.) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-6 in 74% yield (light yellow solid).

Characterization data: $^1$H NMR (500 MHz, DMSO-d$_6$) δ 12.13 (s, 1H), 8.44 (s, 1H), 8.27 (d, J=7.4 Hz, 1H), 8.14 (s, 1H), 7.69 (t, J=7.4 Hz, 1H), 7.43-7.34 (m, 2H); $^{13}$C NMR (126 MHz, DMSO-d$_6$) δ 150.3, 146.4, 143.6, 137.9, 133.4, 130.5, 128.0, 126.1, 125.1, 124.1, 120.8, 116.5, 116.2, 111.8; HRMS m/z (ESI-TOF) calcd for C$_{14}$H$_8$Cl$_2$N$_3$O (M$^+$H)$^+$ 304.0039, found 304.0037.

Example 7

The structural formula of the benzimidazoquinazolinone compound prepared in this embodiment is as follows:

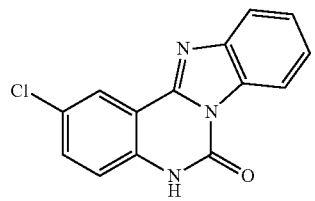

III-7

To a 25 mL sealed tube equipped with a magnetic stirring bar was added N-(4-chloro-2-Formylphenyl)-2-oxo-2-phenylacetamide (0.23 mmol, 66.0 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-7 in 74% yield (light yellow solid).

Characterization data: $^1$H NMR (400 MHz, DMSO-d$_6$) δ 12.10 (s, 1H), 8.36 (d, J=7.4 Hz, 1H), 8.26 (d, J=2.3 Hz, 1H), 7.88 (d, J=7.3 Hz, 1H), 7.71 (dd, J=8.7, 2.4 Hz, 1H), 7.55-7.45 (m, 2H), 7.41 (d, J=8.8 Hz, 1H); $^{13}$C NMR (101 MHz, DMSO-d$_6$) δ 147.1, 146.6, 143.8, 136.5, 132.6, 131.1, 127.7, 125.7, 124.5, 123.8, 119.8, 118.4, 115.3, 113.8.

Example 8

The structural formula of the benzimidazoquinazolinone compound prepared in this embodiment is as follows:

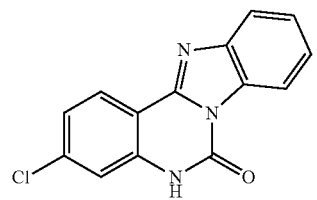

III-8

To a 25 mL sealed tube equipped with a magnetic stirring bar was added N-(3-chloro-2-Formylphenyl)-2-oxo-2-phenylacetamide (0.23 mmol, 66.0 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-8 in 62% yield (light yellow solid).

Characterization data: $^1$H NMR (400 MHz, DMSO-d$_6$) δ 12.06 (s, 1H), 8.41-8.21 (m, 2H), 7.86 (s, 1H), 7.62-7.19 (m, 4H); $^{13}$C NMR (101 MHz, DMSO-d$_6$) δ 147.4, 146.7, 143.9, 138.7, 136.8, 131.0, 126.7, 125.6, 124.4, 123.9, 119.7, 115.7, 115.2, 111.3.

Example 9

The structural formula of the benzimidazoquinazolinone compound prepared in this embodiment is as follows:

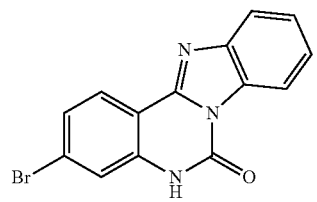

III-9

To a 25 mL sealed tube equipped with a magnetic stirring bar was added N-(3-bromo-2-Formylphenyl)-2-oxo-2-phenylacetamide (0.23 mmol, 76.1 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-9 in 60% yield (light yellow solid).

Characterization data: $^1$H NMR (400 MHz, DMSO-d$_6$) δ 12.04 (s, 1H), 8.34 (d, J=7.5 Hz, 1H), 8.21 (d, J=8.2 Hz, 1H), 7.86 (d, J=7.7 Hz, 1H), 7.58-7.42 (m, 4H); $^{13}$C NMR (101

MHz, DMSO-d$_6$) δ 147.5, 146.7, 143.9, 138.8, 131.0, 126.7, 126.7, 125.6, 125.4, 124.4, 119.7, 118.7, 115.2, 111.60.

Example 10

The structural formula of the benzimidazoquinazolinone compound prepared in this embodiment is as follows:

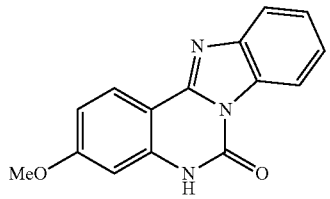

III-10

To a 25 mL sealed tube equipped with a magnetic stirring bar was added N-(2-Formyl-3-methoxy phenyl)-2-oxo-2-phenylacetamide (0.23 mmol, 65.1 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-10 in 70% yield (light yellow solid).

Characterization data: $^1$H NMR (400 MHz, DMSO-d$_6$) δ 11.85 (s, 1H), 8.31 (d, J=7.8 Hz, 1H), 8.19 (d, J=8.8 Hz, 1H), 7.80 (d, J=7.9 Hz, 1H), 7.52-7.35 (m, 2H), 6.96 (dd, J=8.8, 2.3 Hz, 1H), 6.88-6.83 (m, 1H), 3.85 (s, 3H); $^{13}$C NMR (101 MHz, DMSO-d$_6$) δ 162.8, 148.2, 147.0, 144.2, 139.4, 131.0, 126.5, 125.3, 123.6, 119.2, 115.0, 111.9, 105.5, 99.8, 56.0.

Example 11

The structural formula of the benzimidazoquinazolinone compound prepared in this embodiment is as follows:

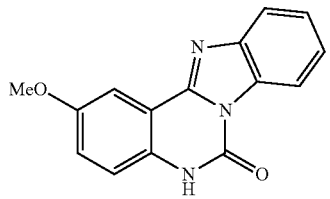

III-11

To a 25 mL sealed tube equipped with a magnetic stirring bar was added N-(2-Formyl-4-methoxy phenyl)-2-oxo-2-phenylacetamide (0.23 mmol, 65.1 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-10 in 70% yield (light yellow solid).

Characterization data: $^1$H NMR (400 MHz, DMSO-d$_6$) δ 11.82 (s, 1H), 8.35 (d, J=7.8 Hz, 1H), 7.83 (d, J=7.8 Hz, 1H), 7.70 (d, J=2.5 Hz, 1H), 7.45 (dt, J=14.9, 7.1 Hz, 2H), 7.34-7.27 (m, 1H), 7.27-7.18 (m, 1H), 3.87 (s, 3H); $^{13}$C NMR (101 MHz, DMSO-d$_6$) δ 155.6, 148.0, 146.6, 143.9, 131.6, 131.2, 125.4, 124.1, 121.5, 119.5, 117.8, 115.3, 112.7, 106.2, 56.0.

Example 12

The structural formula of the benzimidazoquinazolinone compound prepared in this embodiment is as follows:

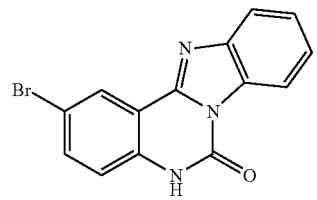

III-12

To a 25 mL sealed tube equipped with a magnetic stirring bar was added N-(4-bromo-2-Formylphenyl)-2-oxo-2-phenylacetamide (0.23 mmol, 76.1 mg), o-Phenylenediamine (0.2 mmol, 21.6 mg) under an atmosphere of air. After the addition of anhydrous DMF (2 mL), the reaction was stirred at 110° C. for 12 h. After cooling to room temperature, anhydrous Cu(OAc)$_2$ (0.02 mmol, 4.0 mg) and Cs$_2$CO$_3$ (0.6 mmol, 195.5 mg) were added into the sealed tube and stirred at 130° C. for additional 12 h. The reaction mixture was extracted with methyl tert-butyl ether (5×30 mL) and washed with brine. The organic phase was dried over anhydrous Na$_2$SO$_4$ and concentrated under reduced pressure. Crude product was purified by flash chromatography on silica gel using PE/EA (PE:EA=5:1), affording the desired product III-12 in 71% yield (light yellow solid).

Characterization data: $^1$H NMR (400 MHz, DMSO-d$_6$) δ 12.05 (s, 1H), 8.41-8.27 (m, 2H), 7.85 (d, J=8.0 Hz, 1H), 7.78 (dd, J=8.7, 2.2 Hz, 1H), 7.52-7.42 (m, 2H), 7.31 (d, J=8.7 Hz, 1H); $^{13}$C NMR (101 MHz, DMSO-d$_6$) δ 146.9, 146.6, 143.8, 136.8, 135.2, 131.1, 126.7, 125.6, 124.5, 119.8, 118.6, 115.4, 115.2, 114.1; HRMS m/z (ESI-TOF) calcd for C$_{14}$H$_8$BrN$_3$O (M$^+$H)$^+$ 313.9923, found 313.9918.

Example 13 Exploration of the Effect of a Catalyst on a Reaction

The benzimidazo[1,2-c]quinazolin-6-one shown as III-1 is prepared when copper acetate is replaced with the copper catalysts shown in Table 1, and other conditions are the same as in Example 1. Reaction results are shown in Table 1.

TABLE 1

Preparation of benzimidazo[1,2-c]quinazolin-6-ones with different catalysts

| Catalyst | Yield (%) |
| --- | --- |
| Cu(Br)$_2$ | 50 |
| CuBr | 45 |

TABLE 1-continued

Preparation of benzimidazo[1,2-c]quinazolin-6-ones with different catalysts

| Catalyst | Yield (%) |
| --- | --- |
| Cu(OTf)$_2$ | 30 |
| CuI | 45 |
| Fe(OTf)$_3$ | Trace (<5) |

Example 14 Exploration of the Effect of the Amount of a Catalyst on a Reaction

The benzimidazo[1,2-c]quinazolin-6-one shown as III-1 is prepared when the amount of the catalyst is replaced with the amounts shown in Table 2, and other conditions are the same as in Example 1. Reaction results are shown in Table 2.

TABLE 2

Preparation of benzimidazo[1,2-c]quinazolin-6-ones with different amounts of the catalyst

| Amount of catalyst | Yield (%) |
| --- | --- |
| Cu(OAC)$_2$/5% | 68 |
| Cu(OAC)$_2$/10% | 81 |
| Cu(OAC)$_2$/15% | 78 |
| Cu(OAC)$_2$/20% | 77 |

Example 15 Exploration of the Effect of Substrate Concentration on a Reaction

The benzimidazo[1,2-c]quinazolin-6-one shown as III-1 is prepared when the amount of DMF is replaced with the addition amounts shown in Table 3, and other conditions are the same as in Example 1. Reaction results are shown in Table 3.

TABLE 3

Preparation of benzimidazo[1,2-c]quinazolin-6-ones with different substrate concentrations

| Amount of DMF (mL) | Yield (%) |
| --- | --- |
| 1 | 65 |
| 2 | 81 |
| 3 | 79 |
| 4 | 75 |

What is claimed is:

1. A synthetic method for benzimidazo[1,2-c]quinazolin-6-ones, having the following route:

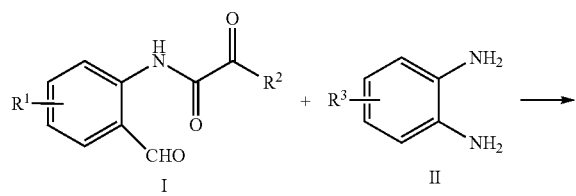

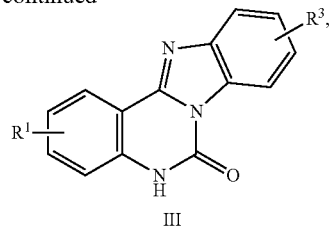

wherein:
$R^1$ is selected from hydrogen, halogen, and C1 to C4 alkoxy,
$R^3$ is selected from C1 to C8 alkyl, halogen, and hydrogen;
$R^2$ is selected from unsubstituted or substituted aryl and unsubstituted aromatic heterocyclic group, and the substituent group on the aryl or aromatic heterocyclic group comprises halogen and alkyl; and
wherein according to the synthetic method, an α-ketoamide compound shown as Formula I and an o-phenylenediamine compound shown as Formula II undergo a reaction in an organic solvent under the action of a catalyst and a base to obtain benzimidazo[1,2-c]quinazolin-6-ones shown as Formula III.

2. The synthetic method according to claim 1, wherein $R^2$ is selected from the group consisting of:

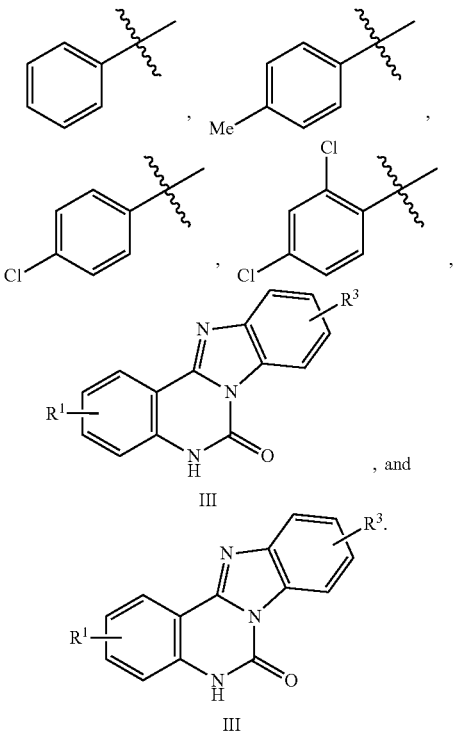

3. The synthetic method according to claim 1, wherein the catalyst is selected from the group consisting of: cuprous iodide, cuprous bromide, copper acetate, copper bromide, copper powder, copper trifluoromethanesulfonate, and anhydrous copper sulfate.

4. The synthetic method according to claim 1, wherein a reaction temperature is 100° C. to 150° C., and a reaction time is 22 to 26 hours.

5. The synthetic method according to claim 1, wherein a ratio of amount of the α-ketoamide compound shown as Formula I to the o-phenylenediamine compound shown as Formula II is 1.0:(0.85-0.95).

6. The synthetic method according to claim 1, wherein a ratio of amount of the α-ketoamide compound shown as Formula I, to the catalyst, and to the base is 1:(0.05-0.15):(2.5-3.5).

7. The synthetic method according to claim 1, wherein based on an amount of the α-ketoamide shown as Formula I, an addition amount of the organic solvent is 6 to 14 mL/mmol.

8. A synthetic method for benzimidazo[1,2-c]quinazolin-6-ones, having the following route:

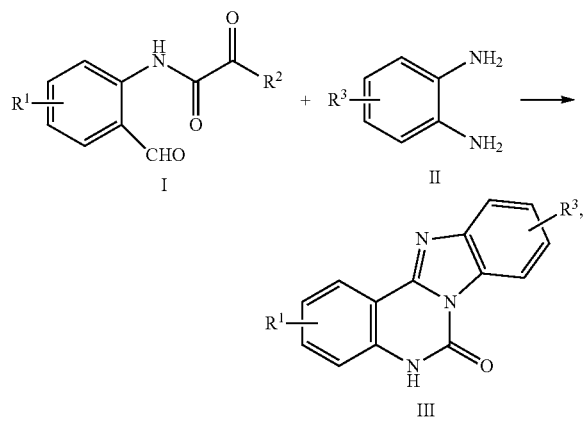

wherein:
1e is selected from hydrogen, halogen, and C1 to C4 alkoxy;
$R^3$ is selected from hydrogen, halogen, and C1 to C4 alkyl;
$R^2$ is unsubstituted phenyl; and
wherein according to the synthetic method, an α-ketoamide compound shown as Formula I and an o-phenylenediamine compound shown as Formula II undergo a reaction in an organic solvent under the action of a catalyst and a base to obtain benzimidazo[1,2-c]quinazolin-6-ones shown as Formula III.

9. The synthetic method according to claim 8, wherein the catalyst is selected from the group consisting of: cuprous iodide, cuprous bromide, copper acetate, copper bromide, copper powder, copper trifluoromethanesulfonate, and anhydrous copper sulfate.

10. The synthetic method according to claim 8, wherein a reaction temperature is 100° C. to 150° C., and a reaction time is 22 to 26 hours.

11. The synthetic method according to claim 8, wherein a ratio of amount of the α-ketoamide compound shown as Formula I to the o-phenylenediamine compound shown as Formula II is 1.0:(0.85-0.95).

12. The synthetic method according to claim 8, wherein a ratio of amount of the α-ketoamide compound shown as Formula I, to the catalyst, and to the base is 1:(0.05-0.15):(2.5-3.5).

13. The synthetic method according to claim 8, wherein based on an amount of the α-ketoamide shown as Formula I, an addition amount of the organic solvent is 6 to 14 mL/mmol.

* * * * *